United States Patent [19]

Mollet et al.

[11] Patent Number: 5,766,904
[45] Date of Patent: Jun. 16, 1998

[54] PHAGE-RESISTANT STREPTOCOCCUS

[75] Inventors: Beat Mollet, Mollie-Margot; David Pridmore; Marie Camille Zwahlen, both of Lausanne, all of Switzerland

[73] Assignee: Nestec S.A., Vevey, Switzerland

[21] Appl. No.: 665,119

[22] Filed: Jun. 14, 1996

[30] Foreign Application Priority Data

Jun. 16, 1995 [EP] European Pat. Off. .............. 95201616

[51] Int. Cl.$^6$ .......................... C12N 1/21; C12N 15/33; C12N 15/66; C12N 15/74
[52] U.S. Cl. .................. 435/172.3; 435/252.3; 435/253.4; 435/320.1; 536/23.1
[58] Field of Search .................... 536/23.1; 435/320.1, 435/172.3, 252.3, 253.4

[56] References Cited

U.S. PATENT DOCUMENTS

| | | | |
|---|---|---|---|
| 4,732,859 | 3/1988 | Hershberger et al. | 435/172.3 X |
| 4,874,616 | 10/1989 | Vedamuthu | 435/172.3 X |
| 4,918,014 | 4/1990 | Vedamuthu | 435/172.3 |
| 5,538,864 | 7/1996 | Hill et al. | 435/69.1 |
| 5,629,182 | 5/1997 | Chopin et al. | 435/172.3 |

FOREIGN PATENT DOCUMENTS 0 246 909   11/1987   European Pat. Off. .
0 474 464 A2   3/1992   European Pat. Off. .

OTHER PUBLICATIONS

J. Bacteriol. (1990), 172(11), 6419-26 Hill, Colin et al. "Cloning, epxression, and sequence determination of a bacteriophae fragment encoding bacteriophage resistance in *Lactococcus lactis*".

Fems Microbiol. lett., vol. 12, No. 11-3.Sep. 1993, pp.87-108, Colin Hill "Bacteriophage abd bacteriophage resistance in lactic acid bacteria".

*Primary Examiner*—Johnny F. Railey, II
*Attorney, Agent, or Firm*—Pennie & Edmonds

[57] ABSTRACT

DNA fragment of phages which are virulent towards a Streptococcus, capable of conferring on a Streptococcus containing it resistance to at least one phage, especially a fragment homologous or hybridizing to the 3.6 kb HindIII fragment present in the plasmid CNCM I-1588 or the 6.5 kb EcoRV fragment present in the plasmid CNCM I-1589. Process for making a Streptococcus resistant to at least one phage, by cloning into a vector a DNA fragment of a phage which is virulent towards a Streptococcus, capable of conferring on a Streptococcus resistance to at least one phage and introducing the vector into a Streptococcus.

10 Claims, 2 Drawing Sheets

PHAGE-RESISTANT STREPTOCOCCUS

TECHNICAL FIELD

The present invention relates to the use of a bacteriophage DNA fragment for making a lactic acid bacterium containing it resistant to bacteriophages.

BACKGROUND

The susceptibility of lactic acid bacteria to a phage attack represents a major problem in the yogurt industry which treats large volumes of milk. Bacteriophages (or phages) can be introduced during the process for the manufacture of yogurt because of a lack of hygiene. They may also appear following the entry into the lytic phase of a lysogenic phage, that is to say a phage integrated into the genome of a bacterium in a latent form. To reduce the incidence of these attacks, industry generally resorts to the use of a mixture of various strains of lactic acid bacteria which are generally resistant to certain phages, or to the use, in rotation for each stage of production, to various strains of lactic acid bacteria. However, these systems have the disadvantage that it is necessary to use different strains of lactic acid bacteria, which leads to the masking of the organoleptic and textural properties of a beneficial strain in relation to the other strains used. It would therefore be particularly advantageous to be able to have means for broadening the resistance spectrum of a strain of beneficial lactic acid bacterium.

Natural resistance of lactic acid bacteria to phages is generally of bacterial origin and involves mechanisms of restriction/modification, of interference with the adsorption of phage particles and/or of abortion of the phage's lytic phase. These resistances are more generally encoded by a bacterial plasmid. Larbi et al. thus describe two strains of *Streptococcus salivarius* subsp. thermophilus (*S. thermophilus*) having at least three bacterial mechanisms of resistance to phages (J. Dairy Res., 59, 349–357, 1992).

These bacterial mechanisms of resistance to phages can be used, moreover, to broaden the spectrum of resistance of lactic acid bacteria to phages. Sing W. D. et al. thus describe the production of clones of *Lactococcus lactis* subsp. lactis (*Lactococcus lactis*) each comprising a different plasmid encoding a bacterial mechanism of resistance to phages (Applied and Environmental Microbiology, 59, 365–372, 1993).

Finally, another potential source of mechanisms of resistance of lactic acid bacteria to phages was recently demonstrated by Hill C. et al. (Journal of Bacteriology, 172, 6419–6426, 1990). DNA fragments of a phage which is virulent towards *Lactococcus lactis* can indeed confer phage resistance on *Lactococcus lactis* containing them. The resistance mechanisms involved are not yet clear. It can, however, be reasonably considered that they are linked to the overproduction or the titration of regulatory signals essential for the development of the phages.

SUMMARY OF THE INVENTION

The aim of the present invention is to provide new DNA fragments of phages capable of conferring phage resistance on a Streptococcus.

To this end, the present invention relates to any DNA fragment of a phage which is virulent towards Streptococci, capable of conferring on a Streptococcus containing it resistance to at least one phage, in particular fragments homologous or hybridizing to the 3.6 kilobase (kb) HindIII DNA fragment present in the plasmid CNCM I-1588 or the 6.5 kb EcoRV DNA fragment present in the plasmid CNCM I-1589.

The invention also relates to a process for making a Streptococcus resistant to at least one phage, by cloning into a vector a DNA fragment of a phage which is virulent towards Streptococci, capable of conferring on a Streptococcus resistance to at least one phage and the recombinant vector is then introduced into a Streptococcus.

The present invention also relates to organisms of the genus Streptococcus comprising, integrated into their genome or by means of a repeatable plasmid, a DNA fragment of a phage which is virulent towards Streptococci, capable of conferring on a Streptococcus resistance to at least one phage, especially a fragment homologous or hybridizing to the 3.6 kb HindIII DNA fragment present in the plasmid CNCM I-1588 or the 6.5 kb EcoRV DNA fragment present in the plasmid CNCM I-1589.

The recombinant replication or integration vectors comprising a DNA fragment according to the present invention are also a subject of the invention.

The Streptococci transformed by a DNA fragment according to the invention have the surprising property of being resistant not only to the phage from which the DNA fragment was isolated, but also to the phages which are homologous to them and even to some phages which are heterologous to them.

The DNA fragments according to the present invention therefore make it possible to considerably broaden the phage resistance spectrum of a Streptococcus. For that, a Streptococcus may be transformed with a vector comprising one or more fragments according to the invention capable of carrying different mechanisms of resistance. A Streptococcus may also be transformed with a vector according to the invention comprising, in addition, one or more bacterial mechanisms of resistance.

Surprisingly, the resistance spectrum conferred by a fragment according to the invention may be different depending on the strain of Streptococcus containing the said fragment.

Finally, it is also possible to envisage developing clones of a beneficial Streptococcus strain each having a different resistance spectrum. These Streptococcus clones could thus be advantageously used in rotation during the industrial fermentation of a milk to manufacture yogurt or cheese.

DETAILED DESCRIPTION OF THE INVENTION

Figure 1:
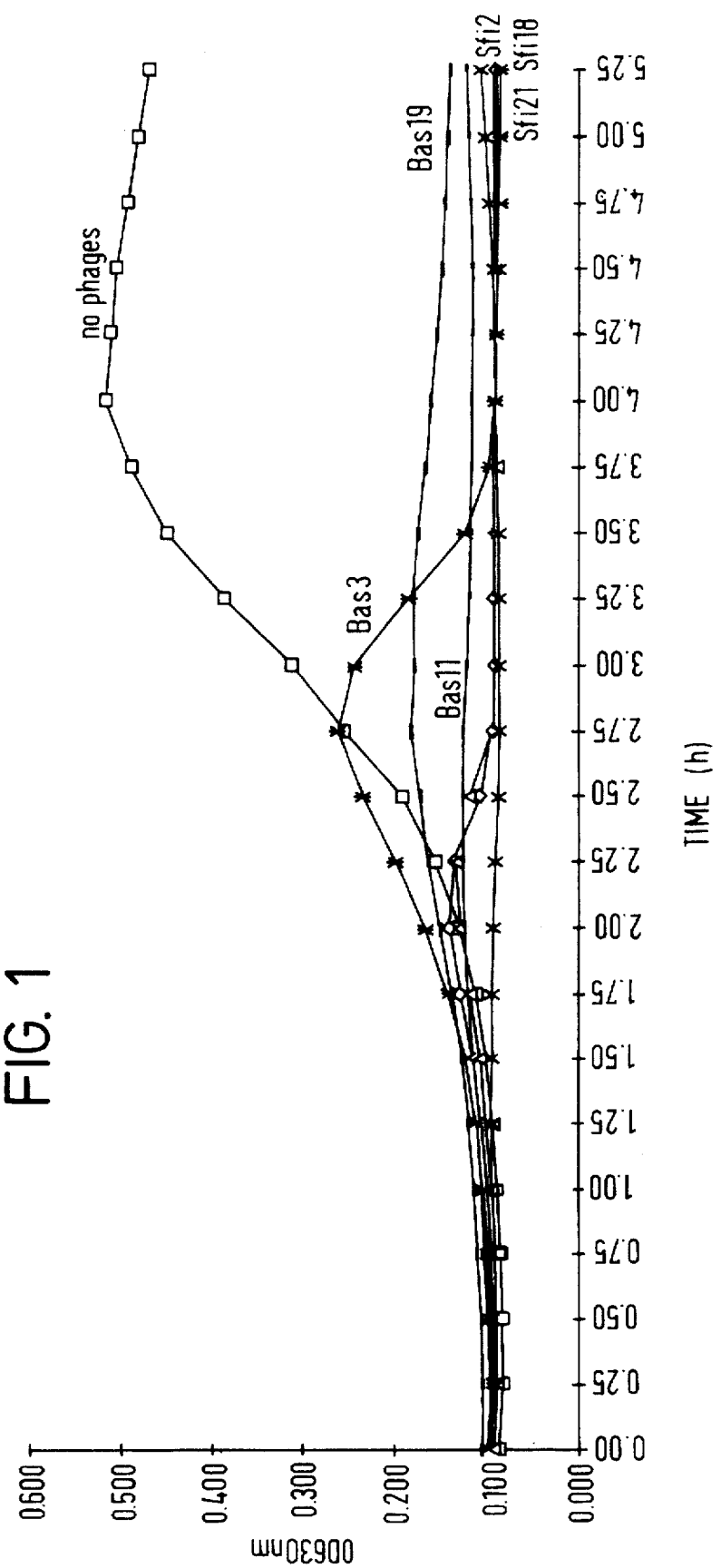

In the description, "homologous phage" is understood to mean the phages which are part of a group of phages which attack the same strains of bacteria and which have a similar lytic behaviour. In contrast, a phage not meeting the two conditions defined above is a heterologous phage.

For the purposes of the present invention, "homologous sequence" is understood to mean any sequence differing from the sequences according to the invention only in the substitution, deletion or addition of a small number of bases. Within this context, two DNA sequences which, because of the degeneracy of the genetic code, encode the same polypeptide will be considered in particular as homologous. A sequence which exhibits more than 80% homology with the sequences according to the invention will also be considered as homologous sequence. In the latter case, the homology is determined by the ratio of the number of bases of a homologous sequence which are identical to those of a sequence according to the invention, to the total number of bases of the said sequence according to the invention.

For the purposes of the present invention, "fragment which hybridizes" is understood to mean any fragment capable of hybridizing with the fragments according to the invention by the Southern-blot method (Sambrook et al., Molecular Cloning, A Laboratory Manual, Cold Spring Harbor Laboratory Press, U.S.A., 1989, chapter 9.31 to 9.58). Preferably, the hybridization is performed under stringent conditions so as to avoid nonspecific or unstable hybridizations.

Finally, the term "fragment" or "DNA fragment" should be understood as a double-stranded DNA fragment of phage origin, which may be synthesized, reproduced in vitro for example by the known method "Polymerase Chain Reaction", or reproduced in vivo in a bacterium of the *Escherichia coli* or *Lactococcus lactis* type, for example.

To carry out a process of selecting a DNA fragment according to the invention, a Streptococci library may be produced which contains phage DNA fragments covering part or all of the genome of a phage. For that, the phage DNA may be digested with a restriction enzyme, the digest is cloned into a vector and then the vectors are introduced into Streptococci, for example.

Next, the transformed Streptococci library may be cultured in a culture medium comprising phages which are virulent towards Streptococci so as to separate a second phage-resistant Streptococci library, for example.

The phage-resistant clones can then be isolated conventionally by plating dilutions of the second library on a solid culture medium, and then selecting among the clones isolated those which exhibit a resistance at least 100 times greater than that of the non-transformed Streptococcus, for example.

As an alternative to the process described above, each phage DNA fragment can also be isolated beforehand by electrophoresis of a phage DNA digest followed by elution of a gel band comprising the fragment of interest. It is then possible to clone each isolated fragment into a vector, to introduce each vector into a Streptococcus, and to select a Streptococcus exhibiting a resistance at least 100 times greater than that of the non-transformed Streptococcus, for example.

To select amongst the resistant Streptococci those which exhibit a resistance at least 100 times greater than that of a non-transformed Streptococcus (by a phage DNA fragment), a dilution of a suspension of virulent phages is preferably plated on a confluent culture, in solid medium, of Streptococci (transformed or otherwise), the number of plaques is counted (each plaque resulting from an infection with one phage), and for a given dilution, the ratio of the number of plaques appearing on a culture of non-transformed Streptococci to that appearing on a culture of transformed Streptococci is determined. A transformed Streptococcus having a ratio of at least 100, preferably a ratio of between $10^3$ and $10^{12}$, can thus be selected.

It was thus possible to isolate from the phage φSfi21, which is particularly virulent towards *S. thermophilus* (Collection du Centre de Recherche Nestlé, Lausanne), a 3.6 kb HindIII DNA fragment. This fragment is present in the plasmid pMZ23 which was deposited, in the form of the strain *S. thermophilus* Sfi1 containing it, on 7 Jun. 1995, at the Collection Nationale de Culture de Microorganisme (C.N.C.M.), Institut Pasteur, 28 rue du Dr Roux, 75724 Paris cedex 15, France, under the provisions of the Budapest Treaty on the International Recognition of the Deposit of Microorganisms for the purposes of Patent Procedure, and comply with the criteria set forth in 37 C.F.R. § 18.01–18.09 regarding availability and permanency of deposits. This deposit was given the deposit number CNCM I-1588. This 3.6 kb HindIII DNA fragment makes it possible to confer on a Streptococcus containing it, especially on an *S. thermophilus*, resistance to the phages which are homologous to the phage from which the DNA fragment was selected, but also resistance to some phages which are heterologous to it.

It was also possible to isolate from the phage φSfi21, which is virulent towards *S. thermophilus* (Collection du Centre de Recherche Nestlé, Lausanne), a 6.5 kb EcoRV DNA fragment. This fragment is present in the plasmid pMZ31 deposited, in the form of the strain *S. thermophilus* Sfi1 containing it, on 7 Jun. 1995 at the C.N.C.M., Institut Pasteur, 28 rue du Dr Roux, 75724 Paris cedex 15, France, under the provisions of the Budapest Treaty on the International Recognition of the Deposit of Microorganisms for the purposes of Patent Procedure, and comply with the criteria set forth in 37 C.F.R. § 1.801–1.809 regarding availability and permanency of deposits. This deposit was given the deposit number CNCM I-1589. It makes it possible to confer on a Streptococcus containing it, especially on an *S. thermophilus*, resistance to at least one phage.

In particular, it was possible to isolate a 0.8 kb EcoRI fragment which is conserved in the abovementioned HindIII and EcoRI fragments. This fragment having the sequence SEQ ID NO:1 which is given in the sequence listing below, has the characteristic feature of being relatively well conserved in phages homologous to the phage φSfi21. It also makes it possible to confer on a Streptococcus containing it, especially on an *S. thermophilus*, resistance to at least one phage.

Given the advantage offered by the 6.5 kb, 3.6 kb and 0.8 kb DNA fragments, and the fact that for the first time DNA fragments of a phage which is virulent towards a Streptococcus have been able to confer resistance on a Streptococcus containing it, the present invention relates to any DNA fragment of phages which are virulent towards a Streptococcus, which is capable of conferring on a Streptococcus resistance to at least one phage.

In particular, the invention may relate to any DNA fragment which, firstly is homologous or which hybridizes to the 3.6 kb HindIII fragment, the 6.5 kb EcoRV fragment and/or the 0.8 kb EcoRI fragment, and secondly is capable of conferring on a Streptococcus resistance to at least one phage. Preferably, fragments are chosen which are at least 20 base pairs (bp) in length, this lower limit being arbitrarily set because the small fragments which hybridize specifically are generally 15–25 bp in length.

To carry out the process for making a Streptococcus resistant to at least one phage, a fragment homologous or hybridizing to the 3.6 kb HindIII fragment present in the plasmid CNCM I-1588 or the 6.5 kb EcoRV fragment present in the plasmid CNCM I-1589 is preferably cloned into a vector. Preferably, the 0.8 kb EcoRI fragment is used.

The vector may be a replicable expression plasmid which may contain replication and expression systems of other microorganisms, such as for example *Escherichia coli* or *Lactococcus lactis*, for example. It may also be an integrative vector. It should also be noted that it is not useful to place upstream of the sequence of the phage, sequences essential for the expression of this sequence, such as for example a Streptococcus promoter.

In the expression or selection process according to the present invention, the vector may be introduced into a bacteria of the genus Streptococcus, especially *S. thermophilus*, by conjugation, transfection or transformation, for example. The organism thus transformed then preferably comprises several copies of the transformed vector.

The present invention is described in greater detail below with the aid of the additional description which will be given below, which refers to examples of obtaining DNA fragments, recombinant plasmids and transformed bacteria according to the invention. It goes without saying, however, that these examples are given by way of illustration of the subject of the invention and do not constitute in any manner a limitation thereto.

The manipulation of DNA, the cloning and the transformation of bacterial cells are, unless otherwise stated, performed according to the procedures described in the above-mentioned book by Sambrook et. al. The percentages are given by weight, unless otherwise indicated.

BRIEF DESCRIPTION OF THE DRAWING FIGURES

FIG. 1: growth curves in a microtitre plate (optical density as a function of time) for the *S. thermophilus* strain Sfi1 transformed with the plasmid pNZ124 in the presence or in the absence of the phages φBas3, φBas11, φBas19, φSfi21, φSfi2 and φSfi18.

Figure 2:
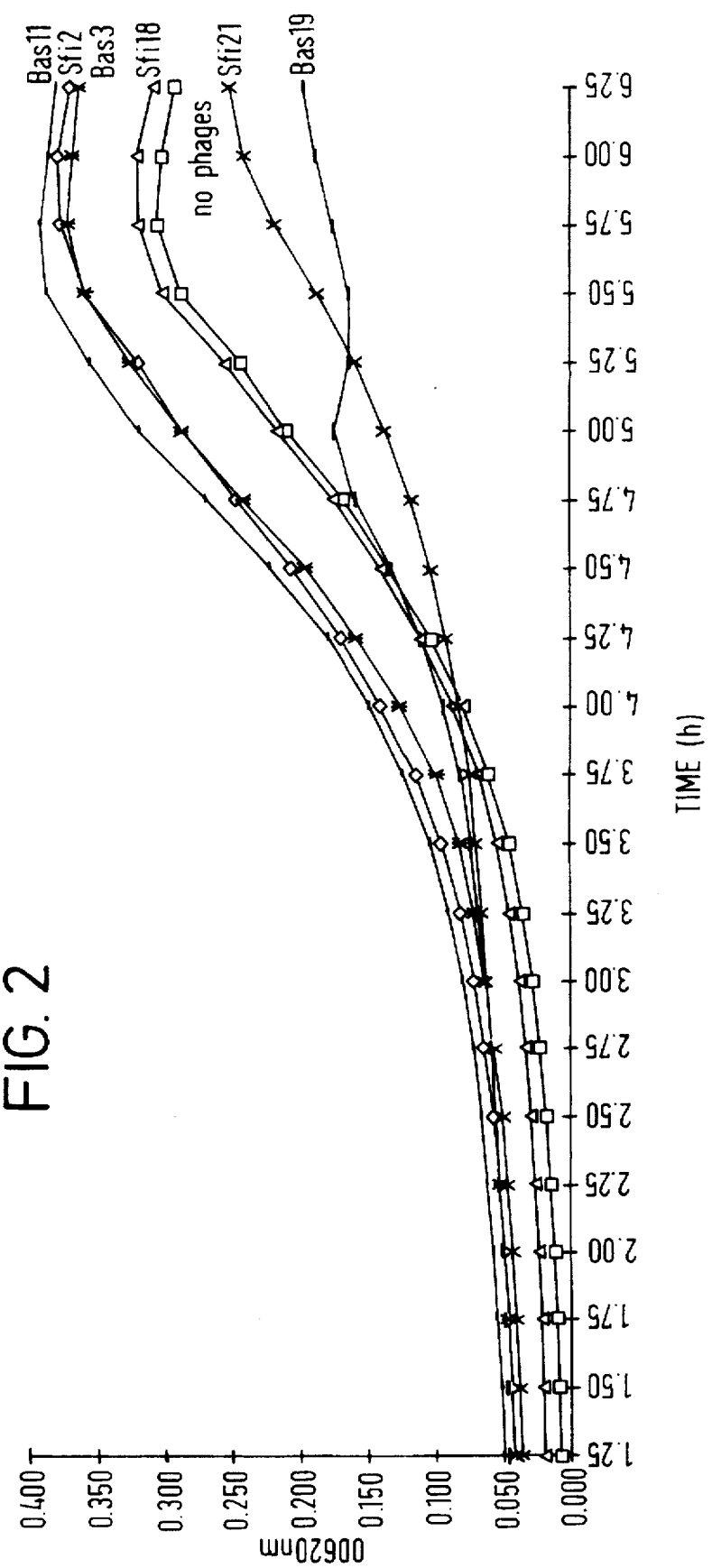

FIG. 2: growth curves in a microtitre plate (optical density as a function of time) for the *S. thermophilus* strain Sfi1 transformed with the plasmid pMZ23 in the presence or in the absence of the phages φBas3, φBas11, φBas19, φBas3, φSfi21, φSfi2 and φSfi18.

EXAMPLES

Media: (add 1.5% Bactoagar for a solid medium)

M17 (Difco, USA) : 0.5% tryptone, 0.5% soytone, 0.5% meat hydrolysate, 0.25% yeast extract, 0.05% ascorbic acid, 0.025% magnesium sulphate, 1.9% disodium beta-glycerophosphate, and water.

LM17: M17 medium comprising 0.5% lactose.

LM17/CaCl$_2$: LM17 medium comprising 0.05% CaCl$_2$.

MSK: skimmed milk (powder reconstituted at 10%) comprising 0.1% yeast extract.

MRS: 1% peptone, 1% hydrolysed meat, 0.5% yeast extract, 0.5% sodium acetate, 0.01% magnesium sulphate, 0.2% dipotassium phosphate, 0.2% ammonium citrate, 0.005% manganese sulphate, 2% dextrose, 0.1% Tween 80, and water.

HJ: 3% tryptone, 0.2% beef extract, 1% yeast extract, 0.4% KH$_2$PO$_4$.

Bacterial strains:

*S. thermophilus* Sfi21 which was deposited on 18 May 1994 at CNCM where it was given the deposit number CNCM I-1424. This strain is sensitive to the phage φSfi21 and is naturally resistant to the phages φBas3, φBas11, φBas19, φSfi2, φSfi9 and φSfi18.

*S. thermophilus* Sfi1 which is sensitive to the phages φBas3, φBas11, φBas19, φSfi2 and φSfi18, and is naturally resistant to the phage φSfi9. Two clones of this strain, containing the plasmid pMZ31- or pMZ24, were deposited at CNCM under the abovementioned deposit numbers CNCM I-1588 and CNCM I-1589.

*S. thermophilus* Sfi9 which was deposited on 18 May 1994 at CNCM where it was given the deposit number CNCM I-1421. This strain is sensitive to the phage φSfi9 and is naturally resistant to the phages φBas11, φBas19, φBas3, φSfi2, φSfi18 and φSfi21.

These three Gram-positive strains have, under a microscope, the appearance of nonflagellate chain-forming cocci. These strains are nonspore-forming and are facultative anaerobes.

Example I

Cloning of DNA Fragments from the Phage φSfi21

I.1. Preparation of DNA fragments from the phage φSfi21:

200 ml of a liquid medium LM17/CaCl$_2$ are inoculated with 1% of a stationary phase culture of the *S. thermophilus* strain Sfi21 and 500 μl of a phage suspension comprising about $10^8$ particles/ml (Collection Nestlé). The medium is incubated at 42° C. until the lysis is complete (about 2 hours), the medium is centrifuged for 30 min at 8000 rpm and at 4° C. in a Sorval SS-34 rotor, the supernatant is recovered and it is recentrifuged in the same rotor for 6 h at 12,000 rpm and at 4° C., then the pellet of phage particles is resuspended in 0.5 ml of a buffer comprising 20 mM Tris pH 7.2, 10 mM NaCl, 10 mM MgSO$_4$. The suspension of phage particles is then stored at −20° C. (this method may also be applied for preparing a suspension of other phages).

The phage suspension is treated with 5 μg/ml of a deoxyribonuclease and 1 μg/ml of a ribonuclease for 30 min at 37° C., 50 mM EDTA and 0.8% SDS are added and the mixture is incubated for 5 min at 37° C., then 100 μg/ml of proteinase K are added and the mixture is incubated for 1 h at 56° C. The proteins are extracted with 1 volume of a phenol solution saturated with TE (100 mM Tris pH 7.5 and 10 mM EDTA), followed by 1 volume of chloroform. The phage DNA present in the aqueous phase is then precipitated in 2 volumes of ethanol comprising 0.3 M sodium acetate pH 5.2 at −70° C. for at least 30 min. The mixture is centrifuged at 13,000 rpm and the pellet of phage DNA is resuspended in 0.4 ml of water.

Part of the solution of phage DNA is then digested traditionally with the restriction enzyme HindIII (Boehringer-Mannheim, Germany) in a buffer comprising 20 mM KCl, 10 mM Tris-HCl pH 8, 10 mM MgCl$_2$, 1 mM DTT and 0.1 mg/ml of BSA. Then under the conditions described above, the proteins are extracted with phenol, the DNA is precipitated and resuspended in the TE solution so as to obtain a solution comprising 100 ng/μl of phage DNA.

I.2. Preparation of a Streptococci library containing DNA fragments covering a large part of the genome of the phage φSfi21:

Under the conditions described above, the vector pNZ124 (from M. De VOS, Agricultural University of Wageningen, The Netherlands) is digested conventionally with the restriction enzyme HindIII. At the end of the reaction, the proteins are extracted with phenol, the DNA is precipitated and resuspended in the TE solution so as to obtain a solution comprising 100 ng/μl of plasmid DNA.

A quantity of the solution of vector pNZ124 (100 ng), another quantity of the solution of DNA fragments (100 ng) and water up to 17 μl are mixed. The mixture is heated for 2 to 5 min at 56° C., then 2 μl of a conventional ligation buffer and 1 μl of a solution of T4 DNA ligase (Boehringer-Mannheim, Germany) are added. At the end of the reaction, the proteins are extracted with phenol, then the DNA is precipitated conventionally.

Competent cells of the *S. thermophilus* Sfi1 strain, which is sensitive to all the phages mentioned in FIGS. 1 and 2, are prepared by the method of Marciset et al., Biotechnology and Bioengineering, 43, 490–496, 1994.

The competent cells are transformed by electroporation with the transformed vectors (Marciset et al.). For that, 200 μl of the suspension of thawed competent cells are mixed with the precipitated pellet of recombinant vectors, the mixture is placed in a cuvette of an electroporation device (Gen Pulser, Biorad), the cuvette is subjected to 2100 V, 25 μF and 400 Ω. 1 ml of the liquid culture medium HJ comprising, in addition, 0.5% lactose is then added and the mixture is incubated at 42° C. for 4 h. The culture is plated on a solid LM17 medium comprising, in addition, 4 μg/ml of chloramphenicol. The bacteria which survive constitute the Streptococci library containing DNA fragments covering the entire genome of the phage φSfi21. It should, however, be noted that some Streptococci contain the vector pNZ124 which is recircularized without incorporating one or more phage fragments.

I.3. Preparation of a library of phage-resistant Streptococci:

The above Streptococci library is cultured in an LM17 liquid culture medium comprising, in addition, 4 μg/ml of chloramphenicol and 100 μl of the suspension of phage φSfi21 particles (point I.1 above). The bacteria which survive constitute the library of phage-resistant Streptococci.

I.4. Analysis of the plasmid pMZ23:

Among the phage-resistant S. thermophilus, it was possible to isolate a clone containing the plasmid pMZ23 which was given the deposit number CNCM I-1588 and which contains a 3.6 kb HindIII phage DNA fragment.

The phage resistance conferred by the plasmid pMZ23 can be determined by a microtitre plate test. For that, the S. thermophilus Sfi1 clone containing the plasmid pMZ23 is cultured in MSK medium supplemented with 4 μg/ml of chloramphenicol. 100 μl of stationary phase culture are diluted with 0.9 ml of LM17/CaCl$_2$ medium supplemented with 4 μg/ml of chloramphenicol. 200 μl of the above medium, 22 μl of the diluted culture and 2.5 μl/ml of the phage φSfi21 suspension above are distributed into the wells of the microtitre plate (in triplicate; 1/100 dilution). The plate is incubated at 42° C. and the optical density is measured at 620–630 nm every 15 min for 7.5 h (Automatic Reader, Dynatech).

The same test was carried out with the phages homologous to the phage φSfi21, that is to say the phages φSfi2, φSfi18 and φBas3, and the phages heterologous to the phage φSfi21, that is to say the phages φBas11 and φBas19. For that, a suspension of these phages was prepared as described in point I.1 above.

For comparison, the same test is performed in parallel with the S. thermophilus Sfi1 strain transformed in the absence of phages. The same test is also performed with the S. thermophilus strain transformed with the plasmid pNZ124.

The results of the tests presented in FIG. 1 show that the S. thermophilus Sfi1 strain transformed with the plasmid pNZ124 is sensitive to all the phages used. The plasmid pNZ124 is not therefore responsible for the resistance.

The results of the tests presented in FIG. 2 show that the S. thermophilus Sfi1 strain transformed with the plasmid pMZ23 is resistant to all the phages used. The 3.6 kb HindIII phage fragment is therefore indeed responsible for the resistance. It makes it possible to confer resistance on the phages homologous and the phages heterologous to the phage φSfi21.

I.5. Evaluation of the degree of resistance:

There are mixed with 0.3 ml of a fresh culture in MSK (supplemented with 4 μg/ml of chloramphenicol) of the S. thermophilus Sfi1 strains transformed with the plasmids pNZ124 or pMZ23, 2.5 ml of MRS-agar medium (0.7% Bactoagar) at 52° C., and 0.1 ml of dilutions of the suspension of each phage evaluated (the phage suspensions are prepared as described in point I.1.). The mixture is plated on an LM17 solid medium supplemented with chloramphenicol, the plates are incubated at 42° C. under anaerobic conditions, and the number of foci of infection is counted on the solid medium (in the form of plaques). For a given dilution, the pNZ124/pMZ23 ratio is then determined by the ratio of the number of plaques on an S. thermophilus culture transformed with pNZ124 to that on an S. thermophilus culture transformed with pMZ23.

The results presented in Table 1 below show that the 3.6 kb HindIII fragment of the phage φSfi21 genome makes it possible to confer resistance to the phages which are homologous to the phage φSfi21.

TABLE 1

| Phages virulent towards S. thermophilus Sfi1 | pNZ124/pMZ23 ratio |
|---|---|
| φSfi21 | $10^5$–$10^7$ |
| φSfi2 (homologous φSfi21) | $>10^7$ |
| φSfi18 (homologous φSfi21) | $>10^7$ |

I.6. Analysis of the 3.6 kb HindIII fragment

With the aim of determining whether parts of the 3.6 kb HindIII fragment could also confer resistance to phages, EcoRI1 fragments of the 3.6 kb HindIII are cloned into pNZ124 and the plasmid is transformed into S. thermophilus Sfi1.

For that, the plasmid pMZ23 is purified and it is cut into fragments with the restriction enzyme HindIII by means known to persons skilled in the art. The DNA fragments are then separated by agarose gel electrophoresis. The band comprising the 3.6 kb fragment is cut out of the gel, the band is deposited on a 0.45 μm centrifugation membrane (MC ultrafree filter) which is stored at −20° C. for 10 min, and the whole is centrifuged for 20 min at 10,000 rpm and at room temperature in a Heraeus Biofuge A centrifuge. The filtrate is extracted with TE-saturated phenol, then the aqueous phase is precipitated with sodium acetate and ethanol at −70° C. for at least 30 min. The mixture is centrifuged at 13,000 rpm, the pellet is resuspended in 0.5 ml of 70% ethanol solution, the suspension is recentrifuged at 13,000 rpm and then the 3.6 kb DNA fragments are resuspended in 10 μl of water.

The 3.6 kb fragment is cut with the restriction enzyme EcoRI, the fragments are ligated to the plasmid pNZ124 previously cut with EcoRI, and the recombinant plasmids are transformed into the S. thermophilus Sfi1strain. The experimental conditions are similar to those presented in point I.1 and I.2 above. The bacteria resistant to the phages φSfi21 are then selected under conditions similar to those presented in point I.3 above, and a particularly resistant clone containing a plasmid pMZ23c comprising a 0.8 kb EcoRI phage DNA fragment is isolated.

The resistance conferred by this fragment on a Streptococcus is evaluated under the conditions presented in point I.4 above. The results presented in Table 2 below show that the 0.8 kb fragment of the genome of the phage φSfi21 makes it possible to confer resistance to phages which are homologous to the phage φSfi21.

TABLE 2

| Phages virulent towards S. thermophilus Sfi1 | pNZ124/pMZ23c ratio |
|---|---|
| φSfi21 | $10^5$ |
| φSfi2 (homologous φSfi21) | $10^3$ |
| φSfi18 (homologous φSfi21) | $>10^{10}$ |

I.7. Sequencing of the 0.8 kb EcoRI fragment:

The plasmid pMZ23c is purified by means known to the person skilled in the art, then the 0.8 kb EcoRI fragment is sequenced by the known method using dideoxynucleotides (Sanger et al., Proc. Natl. Acad. Sci., 74, 5463–5467, 1977). For that, oligonucleotides serving as primer are used which hybridize to the sequences derived from the plasmid pNZ124, on either side of the phage sequence.

The results show that the 0.8 kb EcoRI fragment has the sequence SEQ ID NO:1 given in the sequence listing below.

Example II

Cloning of the 6.5 kb EcoRV DNA Fragment from the Phase φSfi2

A library of *S. thermophilus* Sfi1 strains containing recombinant plasmids pNZ124 comprising EcoRV fragments from the genome of the phage φSfi2 is prepared. For that, a method similar to that described in points I.1 and I.2 above is used.

A library of phage-resistant *S. thermophilus* Sfi1 strains is then prepared as described in point I.3 above. Among the phage-resistant *S. thermophilus*, it was possible to isolate a clone containing the plasmid pMZ31 which was given the deposit number CNCM I-1589 which contains a 6.5 kb EcoRV phage DNA fragment.

The phage resistance conferred by the plasmid pMZ31 can also be determined by tests similar to those described in points I.4 and I.5 above.

Parts of the 6.5 kb EcoRV fragment can also confer resistance to the phages on a Streptococcus containing it. For that, by a method similar to that described in point I.6 above, the plasmid pMZ31 is purified, is cut into fragments with the aid of various restriction enzymes, these fragments are subcloned into the plasmid pNZ124 and *S. thermophilus* Sfi1 is transformed with the recombinant vectors (termed pMZ31 fragment). Finally, transformed bacteria exhibiting phage resistance are selected, by means of the test described in point I.5 above. In particular, bacteria are selected which have a "pNZ124/pMZ31-fragment" ratio greater than 100. This ratio is determined by the number of plaques on an *S. thermophilus* culture transformed with pNZ124 and that on an *S. thermophilus* culture transformed with pMZ31-fragment.

The results presented in Table 3 below show that four fragments derived from the 6.5 kb EcoRV fragment can confer a very good resistance on a Streptococcus, namely the 3 kb EcoRV-BglII, 2 kb BglII-HIII, 3.5 kb BglII-EcoRV and 0.8 kb EcoRI-EcoRI fragments.

TABLE 3

| Phage DNA fragment in *S. thermophilus* Sfi1 | Phage(s) used for evaluating the degree of resistance (see point I.6 above) | pNZ124/pMZ31-fragment ratio (see point I.6 above) |
| --- | --- | --- |
| 6.5 kb EcoRV-EcoRV | φSfi2 | 300 |
| 3 kb EcoRV-BglII | φSfi2 | $10^8$ |

TABLE 3-continued

| Phage DNA fragment in *S. thermophilus* Sfi1 | Phage(s) used for evaluating the degree of resistance (see point I.6 above) | pNZ124/pMZ31-fragment ratio (see point I.6 above) |
| --- | --- | --- |
|  | φSfi18 | $>10^{10}$ |
|  | φSfi21 | $10^7$ |
| 2 kb BglII-HIII | φSfi2 | $2.6 \times 10^5$ |
| 3.5 kb BglII-EcoRV | φSfi2 | $3 \times 10^6$ |
| 0.8 kb EcoRI-EcoRI | φSfi2 | $>10^7$ |
|  | φSfi18 | $>10^{10}$ |
|  | φSfi21 | $>10^7$ |

It can be observed that the resistance conferred on *S. thermophilus* Sfi1 may be different between the fragments, even if the latter have identical parts of nucleic sequences. Indeed, the 3.5 kb BglII-EcoRV fragment contains the 2 kb BglII-HIII fragment, and the 3 kb EcoRV-BglII fragment contains the 0.8 kb EcoRI-EcoRI fragment.

Furthermore, the sequencing of the 0.8 kb EcoRI-EcoRI fragment by the dideoxynucleotide method reveals a sequence identical to the sequence SEQ ID NO:1. The *S. thermophilus* Sfi1 strain containing the plasmid pMZ31-[EcoRI-EcoRI of 0.8 kb], when subjected to attacks by the phages described in FIG. 2, shows growth curves very similar to those obtained under the same conditions for the *S. thermophilus* Sfi1 strain containing the plasmid pMZ23c.

Example III

The plasmid pMZ23 is transformed by electroporation into the *S. thermophilus* Sfi9 strain. For that, a method similar to that described in point I.2 above is used. The evaluation of the resistance spectrum of the transformed strain by a test similar to that described in point I.5 above shows that the transformed *S. thermophilus* Sfi9 strain is resistant to the phage φSfi9 which is a phage heterologous to the phages φSfi21 and φSfi2.

Example IV

A frozen starter of *S. thermophilus* Sfi1 and pMZ23-transformed *S. thermophilus* Sfi1 strains is prepared by inoculating a sterile reconstituted milk at the rate of 1% of a preculture (in MSK medium) of each strain taken at the stage of coagulation of the medium, by incubating the milk at a temperature of about 42° C. until a pH of 5.1 is obtained, by cooling it down to a temperature of 4° C., then by freezing it at −75° C.

Set yogurts are prepared by direct inoculation as a mixture of the frozen starters. For that, a pasteurized reconstituted milk (3.7% fat and 2.5% skimmed milk powder) is inoculated with 6 ml of each frozen starter, the mixture is incubated until a pH of about 4.65 is obtained, and then it is cooled down to 4° C.

SEQUENCE LISTING ( 1 ) GENERAL INFORMATION:

( i i i ) NUMBER OF SEQUENCES: 1

-continued ( 2 ) INFORMATION FOR SEQ ID NO:1:

( i ) SEQUENCE CHARACTERISTICS:
        ( A ) LENGTH: 856 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAATTCAAGG AAGAAAATAA CACAGTTTAT AAATTCCTTA ATGAATATTT GTCAGATGTC      60
GTTTCCACTC GTATTCCAGT TAGATTCTTG TGGGATGTAT ACCGCTCATG GTGTCACGAG     120
GGTAATCATA CTATCCCTAA AAAATCTAAC TTTGAAAAAG AGTTGGCACA GAATTTACCA     180
GTTGGTTGGA TAAAAGATAG ACAAAAACCT CTTGATTTTT TTAACCCAAC TAAAGATAAG     240
CCAGTTTATT GGCATGATTT CAATTTTAAT TGGGACGAAA ACGAGGCGAA GAAAGCAGCA     300
GTAGTGGTTA TGGTTACTCA GTAACCGCAG GTTATTGCAA CAAGTAACCG TAAAACCCAT     360
TGAAAATAAA GGGTTTCGGT TGCTTAGTT  ACTTAGTTAC TACTTTTAAA TATATTTATA     420
AATAAATAAA TAAATAAATA AATATATATA GAGAGAGACT TAAAAAAACG TGTAACTAAG     480
TAACTAAAGT GGCCAGAAAC CTTGATATAT AAGGGGTTTG CGGTGGTTAC GAGTAAAAGT     540
AACTGTTACT GTAATCGAGT AACAAAGGA  GAAAAAAATG GAAATTCAAT ACTTAGAGAT     600
TAATCAAGAA CACGAACCTA ATGAAAATAT TAGTAATTAC ATCAAAGATT TTTCTGAAGC     660
GGCAACAGTT ATAGATGTGC AATGCAACGC TATTCCGGTA CATTTTGAAA AGGTTGGAGA     720
AGACTATTGG ATCGATGAAG ATTATGGCAT TAAAGTTGTT GCGTTATCA  AATATGAAGA     780
TAACAAAGAG GCAACTCCAG AAAAGAAACA ATGGTTGAAG GAATTCAGTC AGATGTCGTT     840
TCCACTCGTA TTCCAG                                                    856
```

What is claimed is:

1. DNA fragment of phages which are virulent towards a Streptococcus, capable of conferring on a Streptococcus containing it resistance to at least one phage, said fragment consisting of the 3.6 kb HindIII fragment present in the plasmid pMZ23, the 6.5 kb EcoRV fragment present in the plasmid pMZ31 or a fragment having the nucleotide sequence of SEQ ID NO:1.

2. DNA fragment of phages which are virulent towards a Streptococcus, said DNA fragment capable of conferring on a Streptococcus containing it resistance to at least one phage, wherein said DNA fragment hybridizes under stringent conditions to the 3.6 kb HindIII fragment present in the plasmid pMZ23, the 6.5 kb EcoRV fragment present in the plasmid pMZ31 or a fragment having the nucleotide sequence of SEQ ID NO:1.

3. Streptococcus having integrated into its genome or by means of a replicable plasmid a DNA fragment according to claim 1.

4. Streptococcus having integrated into its genome or by means of a replicable plasmid a DNA fragment according to claim 2.

5. Recombinant replicating or integrative vector comprising a DNA fragment according to claim 1.

6. Recombinant replicating or integrative vector comprising a DNA fragment according to claim 2.

7. Process for making a Streptococcus resistant to at least one phage, which comprises cloning a DNA fragment according to claim 1 into a vector to form a vector construct and introducing the vector construct into a Streptococcus.

8. Process for making a Streptococcus resistant to at least one phage, which comprises cloning a DNA fragment according to claim 2 into a vector to form a vector construct, and introducing the vector construct into a Streptococcus.

9. Phage resistant Streptococcus produced by the process of claim 7.

10. Phage resistant Streptococcus produced by the process of claim 8.

* * * * *